US006616662B2

United States Patent
Scholer et al.

(10) Patent No.: US 6,616,662 B2
(45) Date of Patent: Sep. 9, 2003

(54) BIPOLAR ENDOSCOPIC INSTRUMENT

(75) Inventors: Uwe Scholer, Hamburg (DE); Dido Arnim Zweibrück, Hamburg (DE)

(73) Assignee: Olympus Winter & IBE GmbH, Hamburg (DE)

( * ) Notice: Subject to any disclaimer, the term of this patent is extended or adjusted under 35 U.S.C. 154(b) by 0 days.

(21) Appl. No.: 10/121,223

(22) Filed: Apr. 12, 2002

(65) Prior Publication Data

US 2002/0151890 A1 Oct. 17, 2002

(51) Int. Cl.[7] ............................................... A61B 18/18
(52) U.S. Cl. ............................ 606/51; 606/48; 606/46
(58) Field of Search ........................... 606/41, 46, 48, 606/52, 205

(56) References Cited

U.S. PATENT DOCUMENTS

| 5,293,878 A | * | 3/1994 | Bales et al. ............... 600/564 |
| 5,396,900 A | * | 3/1995 | Slater et al. .............. 600/564 |
| 5,556,416 A | * | 9/1996 | Clark et al. ............... 606/205 |
| 5,637,110 A | * | 6/1997 | Pennybacker et al. ........ 606/46 |
| 2002/0128649 A1 | * | 9/2002 | Bacher et al. ............. 606/46 |

FOREIGN PATENT DOCUMENTS

| EP | 0624348 | * | 11/1994 |
| FR | 2680314 | * | 8/1991 |

* cited by examiner

Primary Examiner—Michael Peffley
(74) Attorney, Agent, or Firm—Rankin, Hill, Porter & Clark

(57) ABSTRACT

A bipolar endoscopic instrument including a tubular stem having a distal end and a proximal end. The stem distal end supports two jaws that are pivotable relative to one another. The proximal end of the tubular stem has a bipolar hf plug inserted therein at an acute angle to a push/pull wire. The plug applies a bipolar output of a high-frequency (hf) voltage source into the inside of the instrument. The inserted end of the hf plug is shaped such that the plug contacts are axially insulated from each other and each plug contact touches an electrically conducting contact element inside the instrument which, in turn, is connected in electrically conducting manner to one of the two jaws. A unit is present inside the instrument and includes the two contact elements and an insulator electrically separating the contact elements. The hf plug engages the insulator while a particular plug contact touches a particular contact element.

7 Claims, 2 Drawing Sheets

BIPOLAR ENDOSCOPIC INSTRUMENT

BACKGROUND OF THE INVENTION

1. Field of the Invention

The present invention generally relates to bipolar endoscopic instruments and, more particularly, to bipolar forceps or tongs.

2. Description of Related Art

A bipolar instrument may be bipolar forceps or tongs of which the arms or jaws make contact with the two terminals of a high-frequency (hf) source. Illustratively bipolar forceps are used to seize and coagulate tissue. However, they also may be bipolar scissors cutting and simultaneously coagulating the cut tissue surfaces.

In general, power is applied from the two output terminals of the hf source, through the proximal instrument end, to the jaws. As regards the above cited bipolar endoscopic instruments, the two output terminals are insulated from each other and, by means of a two-contact hf plug, are connected to the inside of the instrument. The end of the hf plug inserted into the instrument is configured such that the two plug contacts are axially shifted from each other, each making contact inside the instrument with a contact element electrically connected to a particular jaw. In general, the hf plug is configured at an acute angle to the thrust and/or pull element or wire, hereafter push/pull wire, and to the proximal instrument end.

The application of output power from the two terminals of the hf source through the two-contact hf plug to the inside of the instrument raises problems. Because of the relative compactness inside the instrument, considerable effort must be devoted to conduct the power from the two hf source terminals through a two-contact hf plug into the instrument inside and to guide this power within the instrument to the distal jaws.

SUMMARY OF THE INVENTION

Accordingly, it is the objective of the present invention to simplify the transition from the hf plug into the inside of a bipolar endoscopic instrument of the above kind.

Inside the instrument of the invention, there is a unit comprising two contact elements configured in axially consecutive manner and electrically insulated from each other by an electric insulator.

The angle and the site of insertion of the hf plug are selected such that the plug, by its applied end, engages the insulator. The applied plug end is configured such that each time one hf source terminal makes contact with one contact element of the unit.

By using the above unit, the two hf source terminals may be connected in a very simple manner through a two-contact hf plug into the inside of the bipolar endoscopic instrument and from there with the contact elements.

In further accordance with the present invention, the two contact elements are cylindrical and are configured longitudinally consecutively on a push/pull element or wire. The insulator is disk-shaped and is configured axially between the two contact elements. Electric connection between the contact elements can be effectively prevented by axially mounting the insulator between them.

In further accordance with the present invention, an insulator electrically separates the two contact elements. Therein the contact elements are tubular and can be configured axially into one another. Again, a bush-like insulator is inserted between the two contact elements in order to preclude electric conduction between them.

The manufacture of the contact elements and of the insulator, furthermore the installation of said unit in the instrument, are simple and easily carried out and therefore also economical.

Advantageously, one contact element of the unit is designed to make contact with the push/pull wire, which in turn also is connected in electrically conducting manner with one jaw. The unit's second contact element is designed such that it contacts the instrument's stem, which in turn is electrically connected to the other jaw. In this manner electrical conduction can be established between the contact elements and the jaws without resort to additional components.

As already mentioned above, the hf plug is inserted at an acute angle to the push/pull wire in order to improve instrument handling. In order to simplify as much as possible the engagement of the hf plug in the insulator and, simultaneously, the contact between plug contacts and contact elements, the unit is fitted at the level of the insulator with a borehole pointing in the direction of the installation angle of the hf plug.

The borehole preferably shall be threaded to receive the hf plug, which in turn is threaded at its installed end. However, the borehole also may be a socket for the plug.

In order to attain electrical connection between plug contacts and contact elements when the hf plug is inserted into the threaded borehole or the socket, the two projecting plug contacts exhibit symmetry of rotation. As a result the insertion of the hf plug into the instrument does not require a precise plug-in position because electrical connection is attained at any plug-in position.

The unit may be in the form of a prefabricated component made up of individual elements. Illustratively, the insulator may be soldered to the two contact elements. However, the individual constituents also may be separate and be separately inserted into the instrument.

BRIEF DESCRIPTION OF THE DRAWINGS

These and further features of the invention will be apparent with reference to the following description and drawings, wherein.

DETAILED DESCRIPTION OF THE PREFERRED EMBODIMENTS

Figure 1:
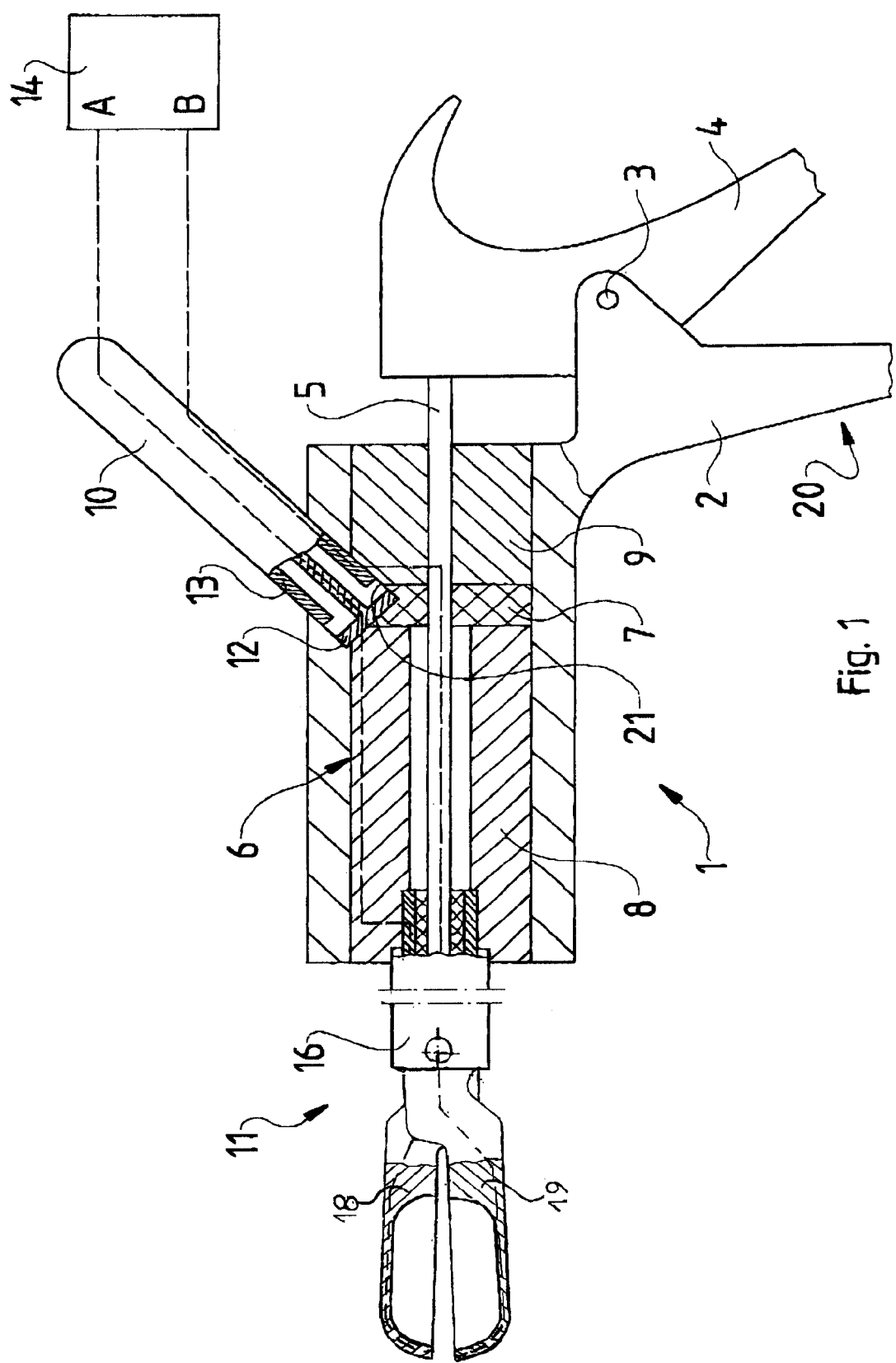
FIG. 1 is a vertical cross-section of the proximal end of a bipolar endoscopic instrument according to a first embodiment of the present invention.

FIG. 1 shows the proximal end of a bipolar endoscopic instrument 1 comprising a stem 11, jaws 18, 19 being mounted at the distal end of the stem. The jaws 18, 19 are electrically connected to the output terminals A, B of an hf source 14.

A handle 20 is present at the proximal end of the instrument 1 and comprises two scissor grips 2 and 4 that pivot relative to each other about a common pivot 3.

The instrument 1 also comprises an axially displaceable push and/or pull wire 5 of which the proximal end is linked to the grip 4 and of which the distal end engages the jaws 18, 19. When the grip 4 is pivoted, the push-pull wire 5 is adjusted axially in the instrument 1 and as a result the jaws pivot relative to each other.

The instrument 1 receives a unit 6 enclosing the push/pull wire 5 and comprising an insulator 7 and two contact elements 8 and 9. A borehole 21 is fitted into the unit 6 and receives the distal end of an hf plug 10. For the sake of clarity, the hf plug is shown in a cross-sectional, schematic manner in the region of its distal end.

Two electrically conducting plug contacts 12 and 13 are on the distal end of the hf plug 10, which in this embodiment has symmetry of rotation. The plug contacts 12 and 13 are connected through mutually insulated conductors (not shown) with the hf-source's output terminals A, B.

The plug 10 is inserted into the borehole 21 of the unit 6 such that the plug contacts 12, 13 are electrically kept apart by the insulator 7 and such that each plug contact 12, 13 makes contact with one contact element 8 and 9 resp., the latter in turn being electrically connected with the push/pull wire 5 resp. the stem 11 fitted with an external insulation 16.

The current from the hf source's terminal A runs from there through the plug contact 12 to the contact element 8 and then to the stem 11 and through the stem 11 as far as one of the distal jaws. The current from the terminal B runs through the plug contact 13 to the contact element 9 and from there to the push/pull wire 5 which is electrically connected to the other distal jaw.

Figure 2:
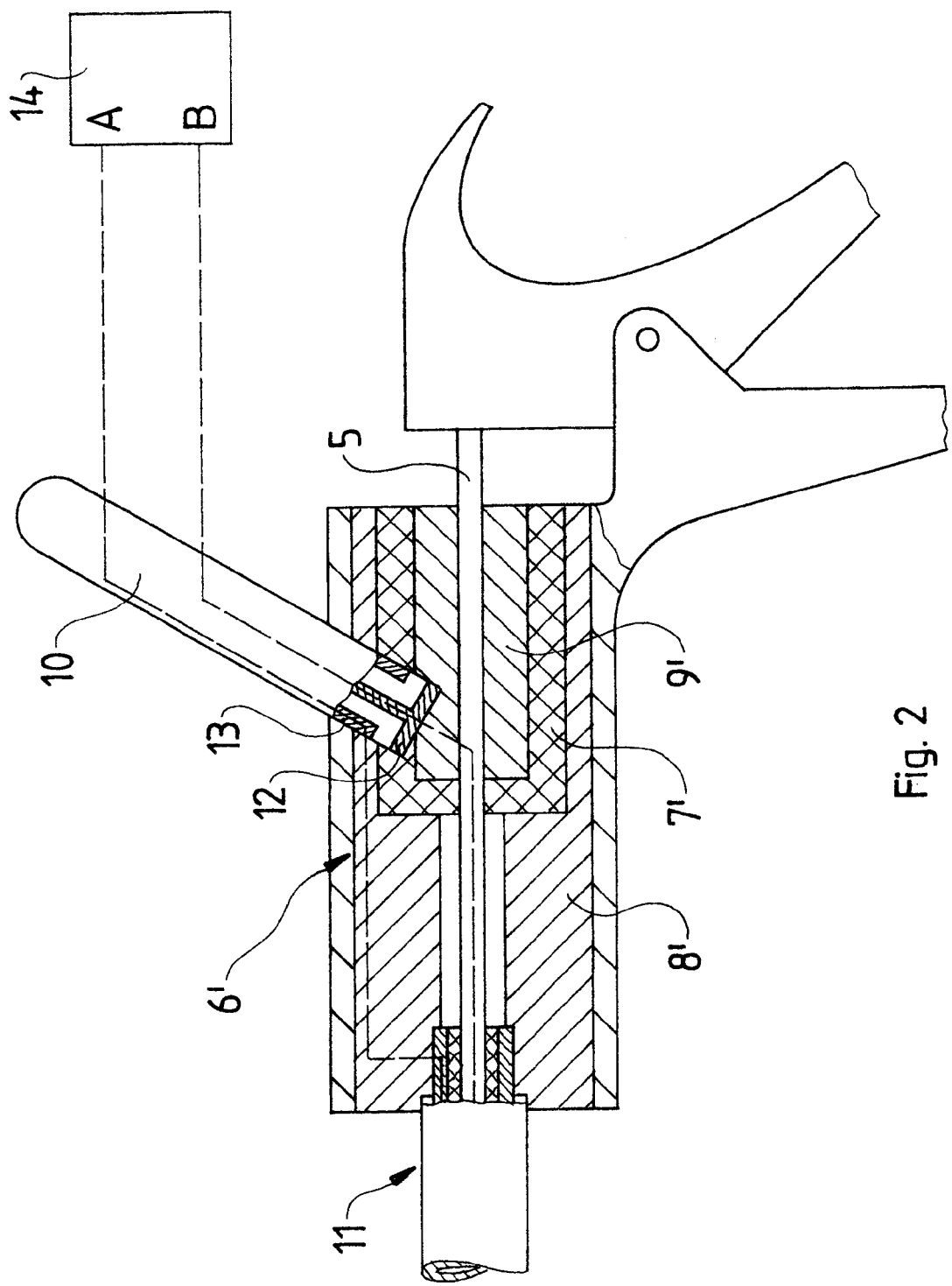
FIG. 2 is a vertical cross-section of the proximal end of a bipolar endoscopic instrument according to a second embodiment of the present invention.

Like FIG. 1, FIG. 2 shows the proximal end of a bipolar endoscopic instrument. However a unit 6' is fitted with a sleeve-shaped contact element 8', which is longitudinally displaceable by the push/pull wire 5 and furthermore receives an inserted cylindrical contact element 9'. An insulator 7' is inserted between the contact elements 8' and 9' and again assumes a cylindrical shape.

In this embodiment the current goes from the output terminal B through the plug contact 12 to the contact element 9' and from there through the push/pull wire 5, which again is electrically connected to one of the distal jaws. The current from the output terminal A runs through the plug contact 13 connected to the contact element 8' through the stem 11 to the other distal jaw.

What is claimed is:

1. A bipolar endoscopic instrument comprising a tubular stem, wherein a distal end of said tubular stem supports two jaws, said jaws being pivotable relative to one another, a proximal end of said tubular stem has a bipolar hf plug inserted therein at an acute angle to a push/pull wire, said plug applying a bipolar output of a high-frequency (hf) voltage source into the inside of said instrument, an inserted end of said hf plug being shaped such that the plug contacts are axially insulated from each other and each plug contact touches an electrically conducting contact element inside the instrument which, in turn, is connected in electrically conducting manner to one of said two jaws, wherein a unit (6, 6') is present inside the instrument (1) and comprises the two contact elements (8, 9, 8', 9') and an insulator (7, 7') electrically separating the contact elements (8, 9, 8', 9'), said unit (6, 6') and the hf plug (10) being designed and mounted in the instrument (1) such that the hf plug (10) engages the insulator (10) and such that a particular plug contact (12, 13) of the hf plug (10) touches a particular contact element (8, 9, 8', 9').

2. The bipolar endoscopic instrument as claimed in claim 1, wherein the contact elements (8, 9) of the unit (6) are cylindrical and are configured consecutively in a longitudinal direction on the push/pull wire (5), the insulator (7) being shaped as a disk and mounted axially between the contact elements.

3. The bipolar endoscopic instrument as claimed in claim 1, wherein the contact elements (8', 9') of the unit (6') are socket-shaped and are mutually inserted longitudinally one in the other on the push/pull wire (5), the insulator (7') also being in the form of a bush and being mounted radially between said contact elements.

4. The bipolar endoscopic instrument as claimed in claim 1, wherein a geometry of the unit (6, 6') is such that one of the contact elements (8, 9, 8', 9') makes contact with one of the jaws via the push/pull wire (5) and the other contact element shall make contact with the other jaw via the tubular stem (11).

5. The bipolar endoscopic element as claimed in claims 1, wherein the unit (6, 6') defines a borehole (21) adjacent the insulator (7, 7') and at the same angle as that subtended between the hf plug (10) and the instrument, the hf plug (10) being received in said borehole (21).

6. The bipolar endoscopic instrument as claimed in claims 1, wherein the plug contacts provided by the hf plug (10) exhibit symmetry of rotation.

7. The bipolar endoscopic instrument as claimed in claim 1, wherein the unit (6, 6') is a component.

* * * * *

UNITED STATES PATENT AND TRADEMARK OFFICE
CERTIFICATE OF CORRECTION

PATENT NO. : 6,616,662 B2 Page 1 of 1
DATED : September 9, 2003
INVENTOR(S) : Scholer et al.

It is certified that error appears in the above-identified patent and that said Letters Patent is hereby corrected as shown below:

<u>Title page,</u>
Insert Item -- [30] Foreign Application Priority Data, April 14, 2001 (DE), 101 18 649.5 --.

Signed and Sealed this

Twenty-seventh Day of January, 2004

JON W. DUDAS
*Acting Director of the United States Patent and Trademark Office*